United States Patent [19]

Oikawa et al.

[11] Patent Number: 5,663,428

[45] Date of Patent: Sep. 2, 1997

[54] METHOD FOR PRODUCING AROMATIC CARBOXYLIC ACIDS

[75] Inventors: Hideo Oikawa; Hiroshi Fukuhara, both of Kuga-gun, Japan

[73] Assignee: Mitsui Petrochemical Industries, Ltd., Tokyo, Japan

[21] Appl. No.: 578,028

[22] Filed: Dec. 26, 1995

[30] Foreign Application Priority Data

Dec. 26, 1994 [JP] Japan ................................. 6-322098

[51] Int. Cl.$^6$ ................................................. C07C 51/265
[52] U.S. Cl. ................................................. 562/416
[58] Field of Search ................................................. 562/416

[56] References Cited

U.S. PATENT DOCUMENTS 4,992,580  2/1991  Partenheimer ........................... 562/416

*Primary Examiner*—Samuel Barts
*Attorney, Agent, or Firm*—Birch, Stewart, Kolasch & Birch, LLP

[57] ABSTRACT

A method for producing aromatic carboxylic acids which comprises oxidizing a starting compound selected from the group consisting of alkyl substituted aromatic hydrocarbons and partially oxidized alkyl substituted aromatic hydrocarbons with a molecular oxygen containing gas in the presence of at least one additive selected from the group consisting of aliphatic hydrocarbons, alicyclic hydrocarbons, aliphatic alcohols, alicyclic alcohols, aldehydes, carboxylic acids and ketones and in the presence of a catalyst comprising a heavy metal compound and a bromine compound in a reaction solvent. The aliphatic alcohols, alicyclic alcohols, aldehydes, carboxylic acids and ketones have ten to thirty carbon atoms in the molecule.

4 Claims, No Drawings

METHOD FOR PRODUCING AROMATIC CARBOXYLIC ACIDS

BACKGROUND OF THE INVENTION

The invention relates to a method for producing aromatic carboxylic acids by oxidizing aromatic hydrocarbons which have alkyl substituents or partially oxidized alkyl substituents.

Aromatic carboxylic acids are one of the important basic chemicals, and are especially useful as raw materials for the production of fibers, resins or plasticizers. By way of examples, terephthalic acid is in wide use as a raw material for the production of polyesters and its demand is recently increasing.

Aromatic carboxylic acids are produced usually by a method in which methyl substituted aromatic hydrocarbons are oxidized by a molecular oxygen containing gas in the presence of a catalyst comprising a heavy metal salt and a bromine compound in an organic solvent such as a lower aliphatic carboxylic acid, for example, acetic acid, in a reactor. However, according to the method, the molecular oxygen containing gas is blown into the liquid phase in which the reaction is carried out so that the liquid phase foams and the volume efficiency of the reactor is small, and hence the method has a problem that the productivity is low.

SUMMARY OF THE INVENTION

It is an object of the invention to provide a method for producing aromatic carboxylic acids in which the foaming of the reaction mixture in a reactor is effectively prevented thereby to improve the volume efficiency of the reactor and the productivity of the production of aromatic carboxylic acids.

The invention provides a method for producing aromatic carboxylic acids which comprises oxidizing a starting compound selected from the group consisting of alkyl substituted aromatic hydrocarbons and partially oxidized alkyl substituted aromatic hydrocarbons with a molecular oxygen containing gas in the presence of at least one additive selected from the group consisting of aliphatic hydrocarbons, alicyclic hydrocarbons, aliphatic alcohols, alicyclic alcohols, aldehydes, carboxylic acids and ketones and in the presence of a catalyst comprising a heavy metal compound and a bromine compound in a reaction solvent.

DESCRIPTION OF THE PREFERRED EMBODIMENTS

The starting compound of which oxidation provides aromatic carboxylic acids usable in the method of the invention is an alkyl substituted or a partially oxidized alkyl substituted aromatic hydrocarbon. The alkyl has 1–4 carbons and may be exemplified by methyl, ethyl, n-propyl or isopropyl, whereas the partially oxidized alkyl may be exemplified by, for example, aldehydo (formyl), acyl, carboxyl or hydroxyalkyl. The starting compound may be mononuclear or polynuclear hydrocarbons.

Accordingly, the alkyl substituted aromatic hydrocarbon may be exemplified by mono- or polyalkylbenzenes which have one to four alkyls each of which has one to four carbons such as toluene, ethylbenzene, n-propylbenzene, cumene, m-diisopropylbenzene, p-diisopropylbenzene, m-cymene, p-cymene, o-xylene, m-xylene, p-xylene, trimethylbenzenes or tetramethylbenzenes; mono- or polyalkylnaphthalenes which have one to four alkyls each of which has one to four carbons such as 1-methylnaphthalene, 2-methylnaphthalene or dimethylnaphthalenes; or mono- or polyalkylbiphenyls which have one to four alkyls each of which has one to four carbons such as methylbiphenyls or dimethylbiphenyls.

In turn, the partially oxidized alkyl substituted aromatic hydrocarbon may be derived from the above mentioned alkyl substituted aromatic hydrocarbon by the partial oxidation of at least one of the alkyls to aldehydo (formyl), acyl, carboxyl or hydroxyalkyl, as above set forth. Accordingly, the partially oxidized alkyl substituted aromatic hydrocarbon may be exemplified by, for example, benzaldehyde, acetophenone, benzyl alcohol, 2-methylbenzaldehyde, 3-methylbenzaldehyde, 4-methylbenzaldehyde, o-toluic acid, m-toluic acid, p-toluic acid, 2-formylbenzoic acid, 3-formylbenzoic acid, 4-formylbenzoic acid or formylnaphthalenes. The alkyl substituted aromatic hydrocarbon or the partially oxidized alkyl substituted aromatic hydrocarbon may be used singly or as a mixture of two or more.

The most preferred starting compound is a dialkylbenzene or a dialkylnaphthalene, in particular, p-xylene which provides terephthalic acid, or diisopropyl-naphthalenes which provide naphthalenedicarboxylic acids by the oxidation according to the method of the invention.

It is preferred that a reaction solvent is used so that the reaction is carried out in a liquid phase according to the invention. The reaction solvent usable includes, for example, water or an aliphatic carboxylic acid having two to four carbons such as acetic acid, propionic acid or butyric acid, or a mixture of these. In particular, a mixture of water and acetic acid is most preferred. The mixture is usually composed of 0.1–20 parts by weight, preferably 1–15 parts by weight, of water, per 100 parts by weight of acetic acid. The reaction solvent is usually used in an amount of 0.5–100 parts by weight, preferably 1–15 parts by weight, per one part by weight of the starting compound used.

It is further preferred that a catalyst is used so that the reaction proceeds at a sufficiently high reaction rate according to the invention. Any known catalyst may be used, however, the most preferred catalyst comprises a heavy metal compound and a bromine compound. As already well known, the heavy metal compound may be a compound of, for example, cobalt, manganese, nickel, chromium, ziconium, copper, lead, hafnium or cerium, and these compounds may be used singly or as a mixture, with a mixture of cobalt and manganese compounds being most preferred.

The heavy metal compound includes, for example, acetates, acetylacetonates or bromides, with acetates being most preferred. The bromine compound usable may be inorganic compounds such as molecular bromine, hydrogen bromide, sodium bromide, potassium bromide, cobalt bromide or manganese bromide, or organic compounds such as methyl bromide, methylene bromide, bromoform, benzyl bromide, bromomethyltoluene, dibromoethane, tribromoethane or tetrabromoethane. These compounds may also be used singly or as a mixture.

It is preferred that the catalyst used in the method of the invention comprises bromine atoms in an amount of 0.05–10 moles, preferably 0.1–2 moles, per mole of a heavy metal atom. The catalyst is used usually in an amount of 10–100000 ppm, preferably 100–50000 ppm, in terms of the concentration of the heavy metal in the reaction solvent.

In the method of the invention, oxygen or air is used as the molecular oxygen containing gas, and among them air is preferred from the practical view point.

The oxidation reaction is carried out usually at a temperature of 100°–250° C., preferably at a temperature of 150°–220° C., under any pressure which maintains the reaction system at a liquid phase.

According to the invention, the alkyl substituted or partially oxidized alkyl substituted aromatic hydrocarbon is oxidized with a molecular oxygen containing gas in the reaction solvent in the presence of at least one additive selected from the group consisting of aliphatic hydrocarbons, alicyclic hydrocarbons, aliphatic alcohols, alicyclic alcohols, aldehydes, carboxylic acids and ketones.

The aliphatic hydrocarbon usable in the method of the invention may be linear or branched, saturated or unsaturated, but preferably it has not less than ten carbon atoms in the molecule. Accordingly, preferred aliphatic hydrocarbons may be exemplified by decane, undecane, dodecane, tridecane, tetradecane, pentadecane, hexadecane, octadecane, eicosane, triacontane, paraffin waxes having various melting points, especially in the range of 20°-100° C., ethylene oligomers or propylene oligomers. The aliphatic hydrocarbon usable in the invention is not specifically limited in the upper limit of the number of carbon atoms, however, it has usually not more than 60 carbon atoms.

The alicyclic hydrocarbon usable has also preferably 10-60 carbon atoms in the molecule, and may be exemplified by butylcyclohexane, decalin, tetralin or liquid paraffin.

The aliphatic alcohols, alicyclic alcohols, aldehydes, carboxylic acids or ketones usable have 10-30 carbons. The carboxylic acids may be mono- or dicarboxylic acids. Some examples of these compounds include, for example, 1-decanol, 2-decanol, 3-decanol, hexadecanol, decanal, 2-decanone, lauric acid, myristic acid, palmitic acid, stearic acid or sebacic acid.

The additive may be used singly or as a mixture. It is preferred that the additive has not less than ten carbon atoms in the molecule as above set forth, however, it may contain compounds of not more than nine carbon atoms.

The additive is used in an amount in the range from 0.1 ppm to 10% by weight, preferably 0.5 ppm to 1% by weight based on the reaction solvent.

The invention will be explained in more detail with reference to examples, however, the invention is not limited thereto.

EXAMPLE 1

An amount of 250 g of acetic acid containing 7% by weight of water, 0.6 g of cobalt acetate tetrahydrate, 0.29 g of manganese acetate tetrahydrate and 0.26 g of 1,1,2,2-tetrabromoethane were placed in an autoclave of titanium having an inside diameter of 66 mm, a depth of 158 mm and a capacity of 500 ml provided with a stirrer, a reflux condenser and a pressure, regulating valve.

The resultant mixture was stirred at a rate of 1500 rpm and heated to a temperature of 190° C. while the pressure was maintained at 13 kg/cm$^2$G. Then a solution of 0.025 g of eicosane in 43 g of p-xylene was added to the mixture over a period of one hour while the air was blown into the mixture at a rate of two liters per minute.

After the completion of addition of p-xylene, when the concentration of oxygen in the waste gas from the autoclave was increased, the supply of air was ceased, followed by cooling the content in the autoclave to room temperature. The content was taken out of the autoclave, and the resultant crystals were collected by filtration, washed with acetic acid and water, and then dried.

The yield of the thus produced terephthalic acid (TA), the content of the by-produced 4-carboxybenzaldehyde (4-CBA) in the terephthalic acid, and the liquid level in the autoclave immediately after the completion of addition of p-xylene are shown in Table 1.

The liquid level was determined as follows by making use of the fact that the temperature of the gas phase was lower than the temperature of the liquid phase. Namely, the temperature difference between the liquid phase and the gas phase in the autoclave was measured with a thermoelectric couple and the liquid level was determined at such a position of the reactor where no difference of temperature was detected between the liquid phase and the gas phase.

COMPARATIVE EXAMPLE 1 p-Xylene was oxidized in the same manner as in Example 1 except that no additive was used. The results are shown in Table 1.

EXAMPLES 2-14 p-Xylene was oxidized in the same manner as in Example 1 except that an additive as shown in Table 1 was used in place of eicosane. The results are shown in Table 1.

TABLE 1

|  | Additive | Amount of Additive (ppm) | Yield of TA (%) | Content of 4-CBA (ppm) | Liquid Level (mm) |
| --- | --- | --- | --- | --- | --- |
| Example 1 | n-Eicosane | 100 | 93.6 | 3200 | 98 |
| Comparative Example 1 | None | — | 93.4 | 3300 | 109 |
| Example 2 | n-Decane | 100 | 94.3 | 3200 | 102 |
| Example 3 | Heptamethylnonane*) | 100 | 93.7 | 3100 | 102 |
| Example 4 | n-Pentadecane | 100 | 93.4 | 3200 | 101 |
| Example 5 | n-Triacontane | 100 | 93.3 | 3200 | 99 |
| Example 6 | Liquid paraffin | 100 | 92.8 | 3200 | 101 |
| Example 7 | Stearyl alcohol | 100 | 93.1 | 3300 | 102 |
| Example 8 | Stearic acid | 100 | 92.9 | 3200 | 102 |
| Example 9 | n-Eicosane | 50 | 93.5 | 3200 | 100 |
| Example 10 | n-Eicosane | 10 | 93.2 | 3300 | 102 |
| Example 11 | Paraffin wax (mp.: 42–44° C.) | 50 | 93.4 | 3200 | 99 |
| Example 12 | Paraffin wax (mp.: 42–44° C.) | 10 | 93.3 | 3200 | 102 |
| Example 13 | Paraffin wax (mp.: 56–58° C.) | 50 | 93.3 | 3200 | 104 |
| Example 14 | Paraffin wax (mp.: 68–70° C.) | 50 | 93.2 | 3300 | 105 |

*)2,2,4,4,6,8,8-Heptamethylnonane

As seen from the results shown in Table 1, the presence of a small amount of additive in the reaction mixture in the oxidation reaction of the starting compound with a molecular oxygen containing gas in a reaction solvent effectively prevents the foaming of the reaction mixture so that the liquid phase is maintained to be low with no adverse effects on the oxidation reaction. Accordingly, the volume efficiency of the reactor is improved, and hence the productivity is improved as well as the production cost is reduced.

A further advantage is that even if the waste gas from the reactor is accompanied by the additive and the waste gas is subjected to usual waste gas treatments, for example, and if the waste gas is burnt as it is or in the presence of a catalyst, the additive neither contaminates a combustion furnace to decrease the combustion efficiency, nor covers the surface of the catalyst to deactivate the catalyst. Namely, the additive has no adverse influence on the treatment of the waste gas generated in the oxidation reaction if the waste gas is accompanied by the additive.

What is claimed is:

1. A method for producing aromatic carboxylic acids which comprises oxidizing a starting compound selected from the group consisting of alkyl substituted aromatic hydrocarbons and partially oxidized alkyl substituted aromatic hydrocarbons with a molecular oxygen containing gas in the presence of at least one additive selected from the group consisting of aliphatic hydrocarbons, alicyclic hydrocarbons, aliphatic alcohols of ten to thirty carbon atoms, alicyclic alcohols of ten to thirty carbon atoms, aldehydes of ten to thirty carbon atoms, carboxylic acids of ten to thirty carbon atoms and ketones of ten to thirty carbon atoms and in the presence of a catalyst comprising a heavy metal compound and a bromine compound in a reaction solvent.

2. The method as claimed in claim 1 wherein the starting compound is a dialkylbenzene or a dialkylnaphthalene.

3. The method as claimed in claim 1 wherein the starting compound is p-xylene.

4. The method as claimed in claim 1 wherein the additive is an aliphatic hydrocarbon or an alicyclic hydrocarbon which has ten to sixty carbon atoms in the molecule.

* * * * *